United States Patent [19]

Miller

[11] Patent Number: 4,786,441

[45] Date of Patent: Nov. 22, 1988

[54] PREPARATION OF IODONIUM AND SULFONIUM TRIFLATES

[75] Inventor: Robert D. Miller, San Jose, Calif.

[73] Assignee: International Business Machines Corporation, Armonk, N.Y.

[21] Appl. No.: 88,779

[22] Filed: Aug. 24, 1987

[51] Int. Cl.[4] .......................................... C07C 143/02
[52] U.S. Cl. ................................................. 260/513 F
[58] Field of Search ..................................... 260/513 F

[56] References Cited

U.S. PATENT DOCUMENTS 4,108,747  8/1978  Crivello ........................ 204/159.18
4,125,555  11/1978  Reineke ........................... 260/456 F

FOREIGN PATENT DOCUMENTS 0024319  2/1982  Japan ................................ 260/513 F Primary Examiner—Alan Siegel
Attorney, Agent, or Firm—Joseph G. Walsh

[57] ABSTRACT

An iodonium or sulfonium triflate is prepared by dissolving or slurring a iodonium or sulfonium halide in an organic solvent and reacting it with a trimethylsilyl triflate.

6 Claims, No Drawings

PREPARATION OF IODONIUM AND SULFONIUM TRIFLATES

TECHNICAL FIELD

The present invention is concerned with a process for the preparation of iodonium and sulfonium triflates.

BACKGROUND OF THE ART

Iodonium and sulfonium triflates are known compounds. Their preparation and uses have been described in the literature. For example, they are described in U.S. Pat. Nos. 4,108,747 and 4,125,555 and the references shown therein.

The prior art methods of preparation involve an exchange reaction between lithinium triflate and the corresponding onium halide with the reaction being an equilibrium one taking place in an aqueous or mixed aqueous-organic medium. There is no force driving the equilibrium reaction in either direction and in general, the process is inefficient.

DISCLOSURE OF THE INVENTION

The present invention provides a cheaper, easier, simpler and faster method of obtaining iodonium and sulfonium triflates in higher yields than previously possible. The process of the present invention also has the additional advantage of providing materials not contaminated by starting materials as is often the case when prior art methods of preparation are employed. According to the present invention, a general procedure for the preparation for iodonium and sulfonium triflates is provided. The corresponding iodonium or sulfonium chloride or bromide is dissolved or slurried within an appropriate organic solvent (such as, methylene chloride) and allowed to react with trimtthylsilyl triflate. It is preferred that the trimethylsilyl triflate be present in a slight molar excess. The reaction is most conveniently carried out at room temperature. The corresponding trimethylsilyl halide is removed by evaporative distillation. (Other sulfonates such as benzene and methane sulfonates can be prepared from the corresponding trimethylsilyl esters using a higher boiling solvent such as 1,2-dichloroethane, which is distilled to remove the TMS halide.) The iodonium triflates thus obtained can be used directly or transformed to the corresponding sulfonium triflates by copper catalyzed decomposition in the presence of sulfides. In this regard, the nonnucleophilic triflate behaves in a similar fashion to the complex metal anions such as $AsF_6-$, $SbF_6-$ etc. This behavior is contrasted with the corresponding iodonium chlorides and bromides which do not form the desired sulfonium salts under the reaction conditions. Using this procedure, the iodonium and sulfonium triflates shown in Table I were prepared in good yield.

TABLE I

| | | mp °C. | % Yield |
|---|---|---|---|
| (1) | ⟨O⟩—I+—⟨O⟩ $O_3SCF_3-$ | 165–8 | 96 |
| (2) | —⟨O⟩—I+—⟨O⟩— $O_3SCF_3-$ | 116–9 | 75 |
| (3) | +⟨O⟩—I+—⟨O⟩+ $O_3SCF_3-$ | 165–7 | 65 |
| (4) | (⟨O⟩—)$_3$ S+ $O_3SCF_3-$ | 134–6 | 80 |
| (5) | —⟨O⟩—S(PH)$_2$+ $O_3SCF_3-$ | 101–3 | 75 |
| (6) | PhCO∧∧S+∨∨ $O_3SCF_3-$ | 38–40 | 83 |

EXAMPLES

The following examples are given solely for purposes of illustration and are not to be considered as limitations to the present invention, many variations of which will occur to those skilled in the art without departing from the spirit or scope thereof.

The corresponding diaryl iodonium chlorides were prepared as described by Crivello and Lam (Macromolecules, 1977, 10, 1307). The phenacyl precursor to the sulfonium triflate 6 was the corresponding sulfonium bromide which was produced by the reaction of dibutyl sulfide with phenacyl bromide.

Diphenyliodonium Triflate 1: Into a 500 mL flask was placed 300 mL of distilled methylene chloride (distilled from $P_2O_5$) and 5.0 g (16 mmol) of commercial diphenyliodonium chloride (Aldrich Chemical Co.). The heterogeneous mixture was stirred vigorously in a water bath at 22° C. and 3.19 ml (3.91 g, 17.6 mmol) of trimethylsilyl triflate was added. The solid dissolved almost immediately but a precipitate reappeared after 5 m. The reaction was stirred for 15 h and the solvent removed on the rotary evaporator. The residue was triturated with ether to yield 6.5 g (96%) of the iodonium triflate 1 (mp 165°–8° C.). The material tested negative for chloride with silver nitrate-ethanol. The aryl iodonium triflates 3 and 4 were produced in a similar fashion.

Triphenylsulfonium Triflate 4: A flask was charged with 2.0 g (4.8 mmol) of diphenyliodonium triflate, 0.93 g (5.0 mmol) diphenyl sulfide and 37 mg of copper benzoate. The mixture was heated under argon for 3 h (bath 125° C.). After cooling, the mixture was triturated with hot ether and stirred 1 h. The solid was filtered and recrystallized from 1:1 butyl acetate-isopropanol (1.6 g, 80%, mp 134°–6° C.).

Di-n-butylphenacyl Sulfonium Triflate -6: Into a flask was placed 691 mg (2 mmol) of di-n-butylphenacyl sulfonium bromide, 10 mL of methylene chloride and 389 mL (2.1 mmol) of trimethylsilyl triflate. The reaction remained homogeneous and stirred 15 h. The solvent was stripped and the residue washed with ether. The solid (g, 83%) slowly crystallized upon pumping to 0.05 mm for 48 h (mp 38°–40° C.).

I claim:

1. A process for preparing an iodonium or sulfonium triflate, said process comprising dissolving or slurring a iodonium or sulfonium halide in an organic solvent and reacting it with trimethylsilyl triflate.

2. A process as claimed in claim 1 wherein the trimethylsilyl triflate is present at about 10% molar excess.

3. A process as claimed in claim 1 wherein the organic solvent is methylene chloride.

4. A process as claimed in claim 1 wherein the organic solvent is 1,2-dichloroethane.

5. A process as claimed in claim 1 wherein the reaction is carried out at room temperature.

6. A process for preparing an iodonium or sulfonium triflate, said process comprising dissolving or slurring a iodonium or sulfonium halide in methylene chloride and reacting it at room temperature with about a 10% molar excess of trimethylsilyl triflate.

* * * * *